(12) United States Patent
Chau et al.

(10) Patent No.: US 8,072,606 B2
(45) Date of Patent: Dec. 6, 2011

(54) FIBER-OPTIC LOCALIZED PLASMON RESONANCE SENSING DEVICE AND SYSTEM THEREOF

(75) Inventors: Lai-Kwan Chau, Chiayi (TW);
Chung-Shi Yang, Taichung (TW);
Wei-Zhe Chang, Chiayi County (TW);
Wei-Te Wu, Taichung (TW)

(73) Assignee: National Chung Cheng University, Chia-Yi (TW)

( * ) Notice: Subject to any disclaimer, the term of this patent is extended or adjusted under 35 U.S.C. 154(b) by 219 days.

(21) Appl. No.: 12/505,975

(22) Filed: Jul. 20, 2009

(65) Prior Publication Data
US 2010/0182607 A1    Jul. 22, 2010

(30) Foreign Application Priority Data

Jan. 20, 2009 (TW) .............................. 98102078 A

(51) Int. Cl.
*G01N 21/55* (2006.01)
(52) U.S. Cl. ....................................... 356/445; 356/446
(58) Field of Classification Search .......... 356/445–448, 356/300–301; 436/501–503; 422/68.1, 50; 702/19, 1; 250/458.1
See application file for complete search history.

(56) References Cited

U.S. PATENT DOCUMENTS

2010/0103421 A1*  4/2010  Johansen et al. .............. 356/367
2010/0195106 A1*  8/2010  Ogawa .......................... 356/445

OTHER PUBLICATIONS

Thesis published on Jul. 22, 2008, Localized Plasmon Resonance Sensors: Comparison of Several Waveguide-based Configurations and Development of pre-filtered Dip Probe, 695260003.

* cited by examiner

*Primary Examiner* — Tri T Ton
(74) *Attorney, Agent, or Firm* — WPAT, P.C.; Anthony King

(57) ABSTRACT

The present invention discloses a fiber-optic localized plasmon resonance (FO-LPR) sensing device and a sensing system thereof, the FO-LPR sensing system includes a light source, a FO-LPR sensing device and a detector, and the light source provides a light beam entered into the FO-LPR sensing device, and the detector generates a detected signal according to an emergent light from the FO-LPR sensing device. The FO-LPR sensing device includes an optical fiber, a noble metal nanoparticle layer and a filter film layer. The filter film layer is having a porous material, and the porous material comes with a pore diameter or a property selected according to a feature of a sample, while an interfering substance in the sample is isolated.

20 Claims, 19 Drawing Sheets

FIBER-OPTIC LOCALIZED PLASMON RESONANCE SENSING DEVICE AND SYSTEM THEREOF

BACKGROUND OF THE INVENTION

1. Field of the Invention

The present invention relates to a sensing device and a sensing system thereof, in particular to a fiber-optic localized plasmon resonance (FO-LPR) sensing device and a system thereof.

2. Description of the Related Art

At present, localized plasmon resonance (LPR) may be used to examine the change of local refractive index at the surface of noble metal nanoparticles, such that if there is a change of the LPR band, the spectral characterstics of an emergent light will be affected. If a suitable recognition unit is provided, its attachment onto a gold nanoparticle surface may be used to analyze a corresponding analyte in a sample, such that the local refractive index sensed by noble metal nanoparticles may be affected to achieve a specific sensing capability. If the noble metal nanoparticle layer (such as gold or silver nanoparticles) is disposed onto an optical fiber, the volume of the sensor may be reduced effectively, and the optical fiber may be used to enhance the variation of LPR signal through multiple total internal inflections, so as to improve the sensitivity of the sensor. In other words, the incident light signal is affected by LPR for each time of the light reflection, and a portion of the light energy is absorbed or scattered. Thus, the more the number of reflections, the greater is the attenuation of light intensity at that frequency, and the effect of enhancing the sensor sensitivity may be achieved. A sensing element developed by the aforementioned optical fiber and the principle of LPR is called a fiber-optic localized plasmon resonance (FO-LPR) sensor. The FO-LPR sensor concurrently has a high sensitivity and selectivity after it is integrated with recognition molecules, and thus the FO-LPR sensor has a high potential to be developed as a chemical and biochemical sensor. In addition, the method of enhancing signals with multiple total internal reflections may be applied to the technology of measuring a surface-enhanced spectrum such as surface-enhanced Raman scattering and surface-enhanced fluorescence.

Although the FO-LPR is highly sensitive and specific and has the real-time detection capability, the sensor must be exposed to a complicated matrix if a real sample is sensed. For example, cell debris, blood cells, and immune cells or even a suspended matter such as dusts and fibers will be attached or deposited onto a surface of the sensor easily, so that the noble metal nanoparticles will have a change of local refractive index at their surfaces caused by the aforementioned surface covering process, so as to produce a serious error of measurement. Therefore, it is necessary to eliminate the non-specific attachment of such large particulate substances in order to use the FO-LPR for sensing an analyte in a real sample.

SUMMARY OF THE INVENTION

Therefore, it is a primary objective of the present invention to overcome the shortcomings of the prior art by providing a FO-LPR sensing device and a sensing system thereof in accordance with the present invention.

To achieve the foregoing objective, the present invention provides a FO-LPR sensing device comprising an optical fiber, a noble metal nanoparticle layer and a filter film layer. The noble metal nanoparticle layer is disposed on the optical fiber, and the filter film layer comprises a porous material and encloses the optical fiber, wherein the porous material comes with a pore diameter or a property selected according to a feature of a sample, while interfering substances in the sample are isolated.

To achieve the foregoing objective, the present invention also provides a FO-LPR sensing device system, comprising a FO-LPR sensing device, a light source and a detector. The FO-LPR sensing device comprises an optical fiber, a noble metal nanoparticle layer and a filter film layer. The noble metal nanoparticle layer is disposed on the optical fiber, and the filter film layer comprises a porous material and encloses the optical fiber, and the light source provides a light beam to be entered to the FO-LPR sensing device, and the detector receives an emergent light from the FO-LPR sensing device to generate a detected signal; wherein the porous material comes with a pore diameter or a property selected according to a feature of a sample, while interfering substances in the samples are isolated.

The FO-LPR sensing device and a sensing system thereof in accordance with the present invention have one or more of the following advantages:

(1) The FO-LPR sensing device and a sensing system thereof rely on the porous material of the filter film layer, so that they may be applied to sense a complicated sample.

(2) The FO-LPR sensing device and a sensing system thereof may be selected according to the feature of a sample, and try to allow the desired analyte to pass through, while unnecessary interfering substances in the sample are isolated.

DETAILED DESCRIPTION OF THE PREFERRED EMBODIMENTS

The original intention of the present invention is to attempt to eliminate the interference of foreign substances in detection of an analyte in a real sample, since the interference may not be eliminated regardless of the selectivity of the sensor by the recognition unit in accordance with the prior art. Although the FO-LPR technology has a certain level of selectivity, yet the interference of a non-specific attachment still exists. To reduce unexpected results of this sort, we enclose a filter film layer around the LPR optical fiber to filter particles according to their molecular size or chemical properties, directly isolate the large particulate interfering substances from a sensing area, and selects a porous material with a semi-permeable property of the filter film layer to allow the desired analyte to enter only. Now, the sensing area of the FO-LPR has a simpler and cleaner working environment. In addition, the filter film layer is preferably in the shape of a hollow tubular column, and the overall volume of the assembled components is preferably minimized.

Figure 1:
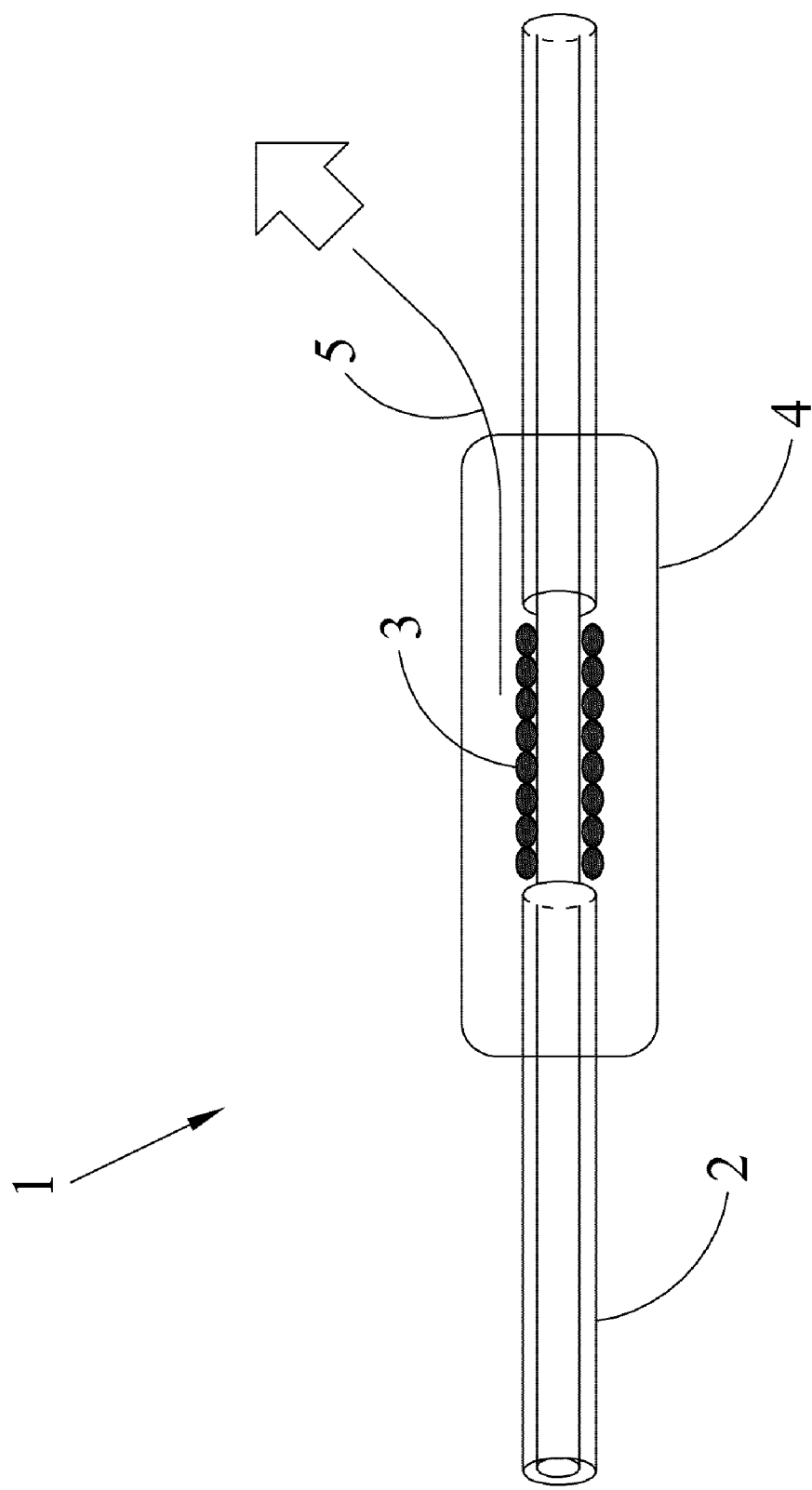
FIG. 1 is a schematic view of a FO-LPR sensing device and its system in accordance with a first preferred embodiment of the present invention.

With reference to FIG. 1 for a schematic view of a FO-LPR sensing device and its system in accordance with a first preferred embodiment of the present invention, the FO-LPR sensing device 1 comprises an optical fiber 2, a noble metal nanoparticle layer 3 and a filter film layer 4, and the optical fiber 2 is a LPR optical fiber, and a region of the optical fiber with the cladding removed is a sensing area, and the noble metal nanoparticle layer 3 is selected from the group consisting of gold nanoparticles and silver nanoparticles, and the shape of the noble metal nanoparticles is spherical, rod-shaped or shell-shaped noble metal nanoparticles. The noble metal nanoparticle layer 3 is disposed on the optical fiber 2, and the filter film layer 4 comprises a porous material and encloses the optical fiber 2. The FO-LPR sensing device 1 further comprises at least one duct 5 and a pump, and the pump draws the sample through the filter film layer 4. This method may enhance the mass transfer rate of introducing an analyte into the sensing region. The analyte is selected from the group consisting of biological molecules and chemical molecules, and the filter film layer 4 is like a filter for filtering and purifying the original complicated sample, wherein the porous material of the filter film layer 4 comes with a pore diameter or a property selected according to a feature of the sample, while interfering substances in the sample are isolated. The filter film layer has a pore density from $4 \times 10^4$ cm$^{-2}$ to $20 \times 10^4$ cm$^{-2}$, a thickness from 50 μm to 100 μm, a molecular weight cut off (MWCO) smaller than or equal to 500 kDa, and a material of polysulfone (PS), cellulose ester (CE), regenerated cellulose (RC), polyethersylfone (PES) and polyarylethersulphone (PAES). The interfering substance is a blood cell, a cell debris, an immune cell, a dust, a fiber, a bacterium, a macromolecule, or a large particulate foreign substance.

Figure 2:
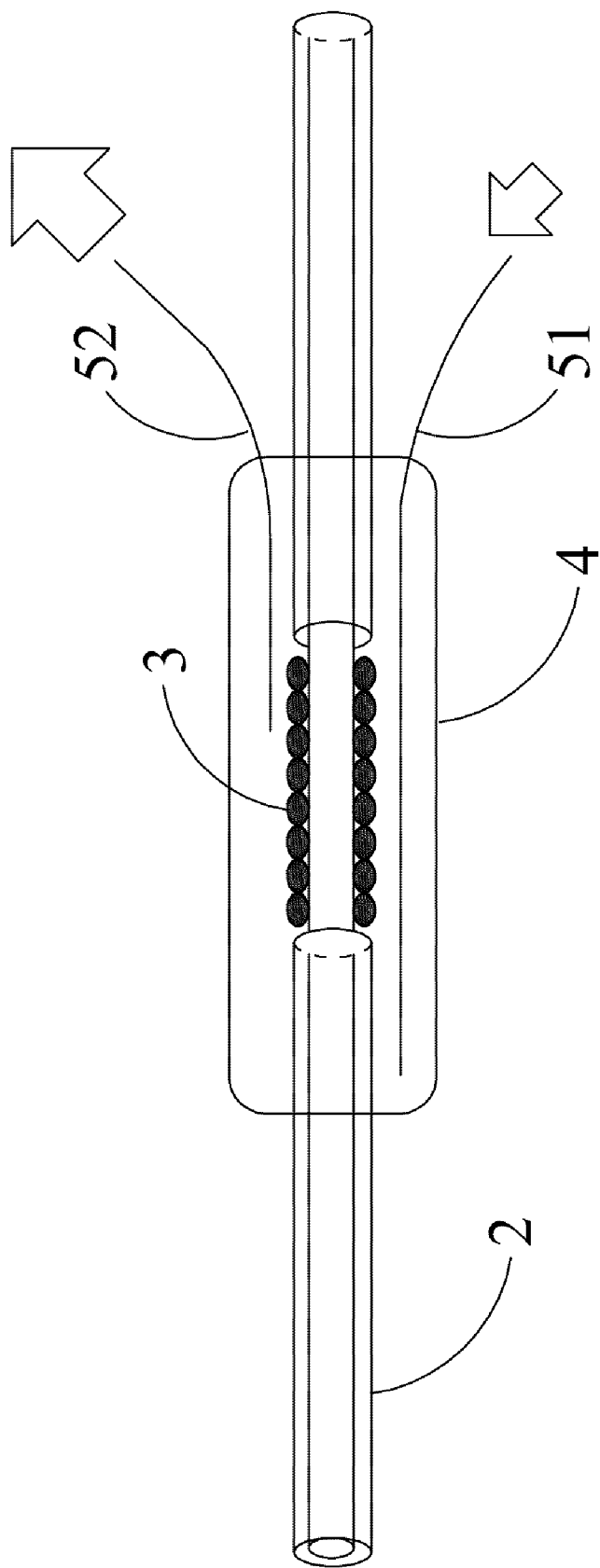
FIG. 2 is a schematic view of a FO-LPR sensing device and its system in accordance with a second preferred embodiment of the present invention.

With reference to FIG. 2 for a schematic view of a FO-LPR sensing device and its system in accordance with a second preferred embodiment of the present invention, the FO-LPR sensing device comprises an optical fiber 2, a noble metal nanoparticle layer 3 and a filter film layer 4. The noble metal nanoparticle layer 3 is disposed on the optical fiber 2, and the filter film layer 4 comprises a porous material and encloses the optical fiber 2. The FO-LPR sensing device further comprises a first duct 51 and a second duct 52 disposed in a region enclosed by the filter film layer 4, and the first duct 51 is used for introducing an input perfusion liquid, and the second duct 52 is used for discharging the output perfusion liquid. The analyte is selected from the group consisting of biological molecules and chemical molecules, and the filter film layer is like a filter for filtering the sample, wherein the porous material of the filter film layer 4 has a pore diameter or a property selected according to a feature of the sample, while interfering substances in the sample are isolated. The FO-LPR sensing device 1 may be applied to a microdialysis, and the microdialysis is mainly designed for sampling a body fluid of a living object. The FO-LPR sensing device 1 has a function similar to an artificial blood vessel that may reduce any harm to cells and tissues caused by the experiment, and the volume of biofluid will not be affected during the sampling process, and thus this device may be used for in vivo or in vitro sampling. When a sample is collected through a microdialysis tube, it is necessary to use two liquid ducts to introduce and discharge the perfusion liquid so that the analyte will be carried to the sensor surface more easily. With the dialysis membrane, high molecular weight proteins or other macromolecules may be isolated by the membrane, and thus the liquid collected by the microdialysis into the sensing region is much pure, and the non-specific attachment of large particulate foreign substances may be reduced significantly. When the FO-LPR sensor carries out in vivo tests, its integration with microdialysis is a good choice.

Figure 3A:
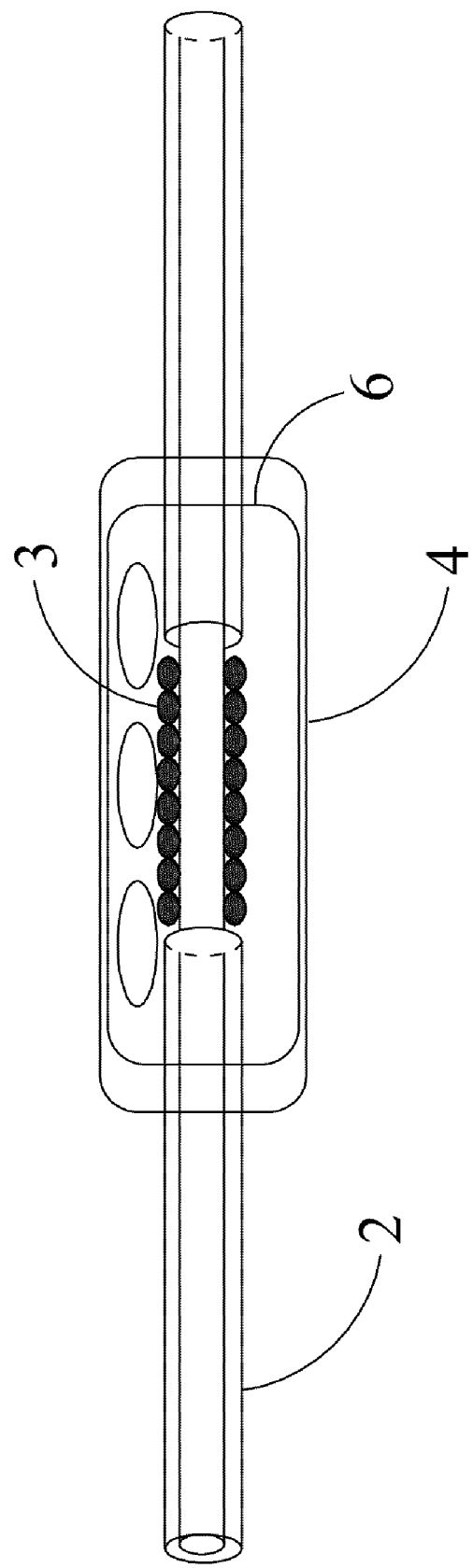
FIG. 3A is a schematic view of a FO-LPR sensing device and its system in accordance with a third preferred embodiment of the present invention.
Figure 3B:
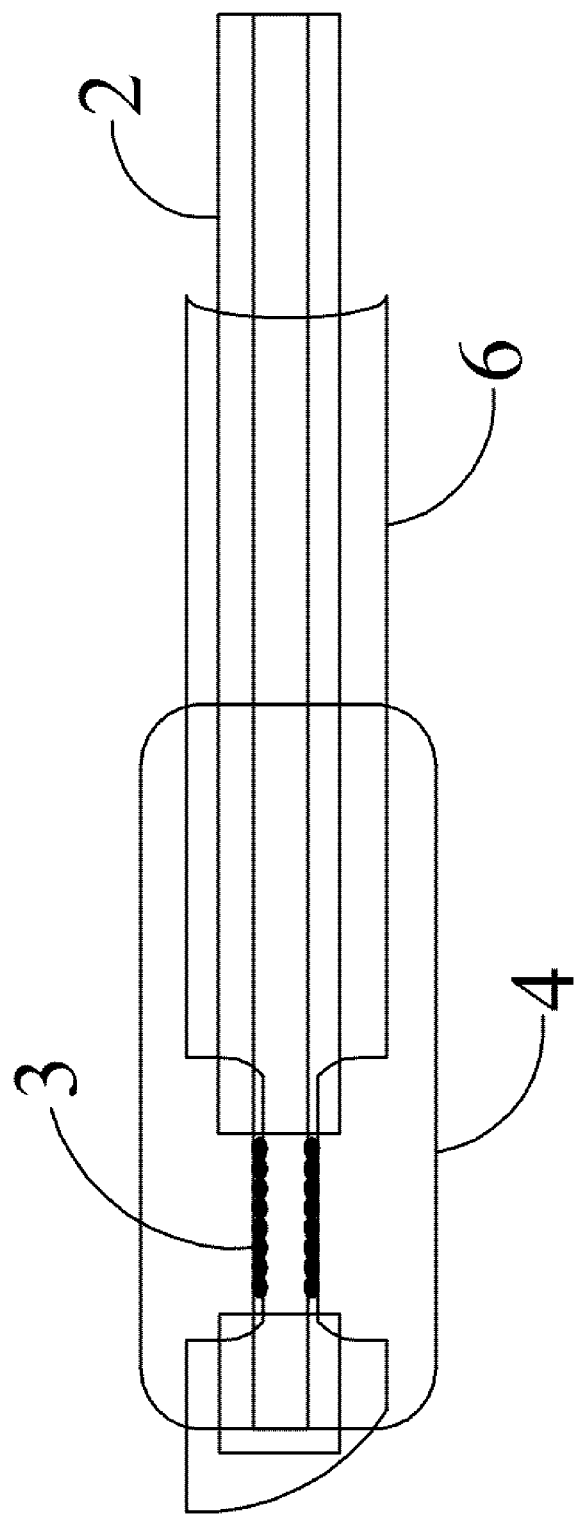
FIG. 3B is a schematic view of a reflection-based fiber-optic plasmon resonance (RFO-LPR) configuration of a FO-LPR sensing device and its system in accordance with a third preferred embodiment of the present invention.

With reference to FIG. 3A for a schematic view of a FO-LPR sensing device and its system in accordance with a third preferred embodiment of the present invention, the FO-LPR sensing device comprises an optical fiber 2, a noble metal nanoparticle layer 3 and a filter film layer 4, the noble metal nanoparticle layer 3 is disposed on the optical fiber 2, and the filter film layer 4 comprises a porous material and encloses the optical fiber 2, and the filter film layer 4 is like a filter for filtering a sample. With the filter film layer 4, large interfering substances originally existed in a sample will be isolated by such a thin layer, so that the the optical fiber 2 may be situated in a simpler environment. In addition, if the chemical properties or pore size of the filter film layer 4 is chosen appropriately, bacteria and debrises may be isolated from the sensing region near the optical fiber 2, not only avoiding contamination of the sample, but also saving the trouble of a disinfection procedure of the FO-LPR sensing device. Since a portion of the cladding of the optical fiber 2 is removed, therefore the optical fiber 2 becomes more fragile and gets broken easily. The filter film layer 4 may be deformed or even covered onto a surface of the sensing area of the optical fiber due to the pressure of external environment or the effect of gravitation. Therefore, an appropriate rigid frame 6 with openings on its wall may be placed between the filter film layer 4 and the optical fiber 2 to provide a good physical support. For example, a hollow steel needle having several small holes with a diameter of approximately 0.5 mm on its wall is a very appropriate choice, but the pore diameter should not be greater than 5 mm to avoid having insufficient mechanical strength. With reference to FIG. 3B for a schematic view of a RFO-LPR configuration of a FO-LPR sensing device and its system in accordance with a third preferred embodiment of the present invention, the configuration is useful as a probe. If a tapered steel needle is used an external sheath for guidance, a RFO-LPR probe may be pierced into a desired object easily. For simplicity, the tapered steel needle with holes may be used as a guider, not only providing a good physical support for the optical fiber 2 and the filter film layer 4, but also guiding them to the desired testing region. If the overall physical strength of the frame is sufficient, the hole is not necessary small and in a circular shape, but may be of a larger area, such as a long slit, so as to achieve the effect of accelerating mass transfer.

Figure 4A:
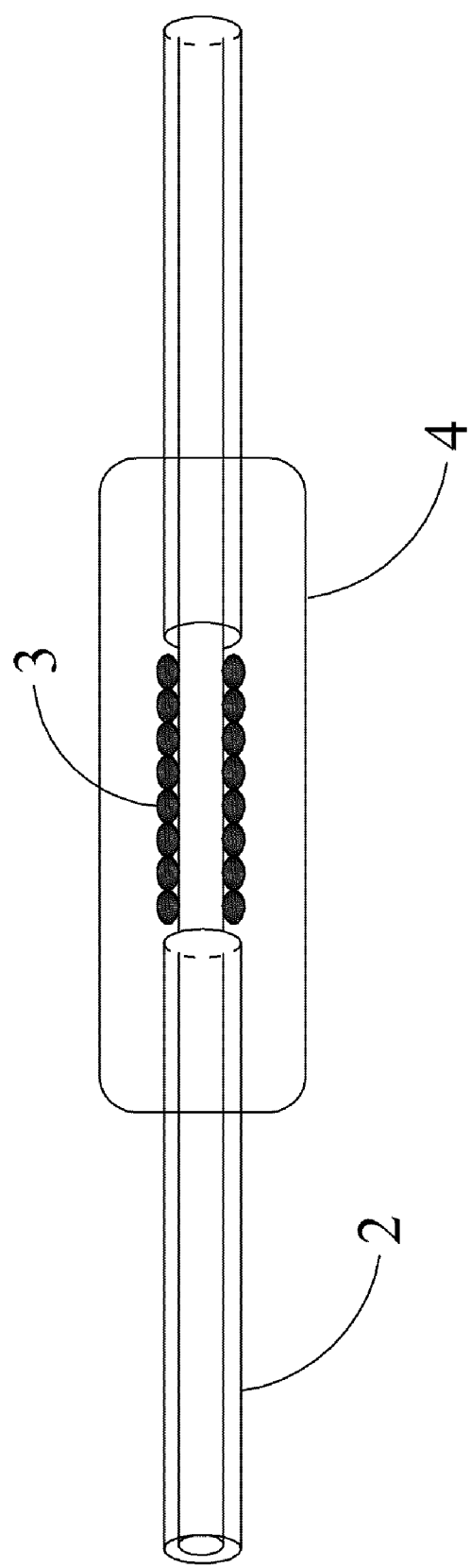
FIG. 4A is a schematic view of totally removing the cladding in a certain region of an optical fiber of a FO-LPR sensing device in accordance with the present invention.
Figure 4B:
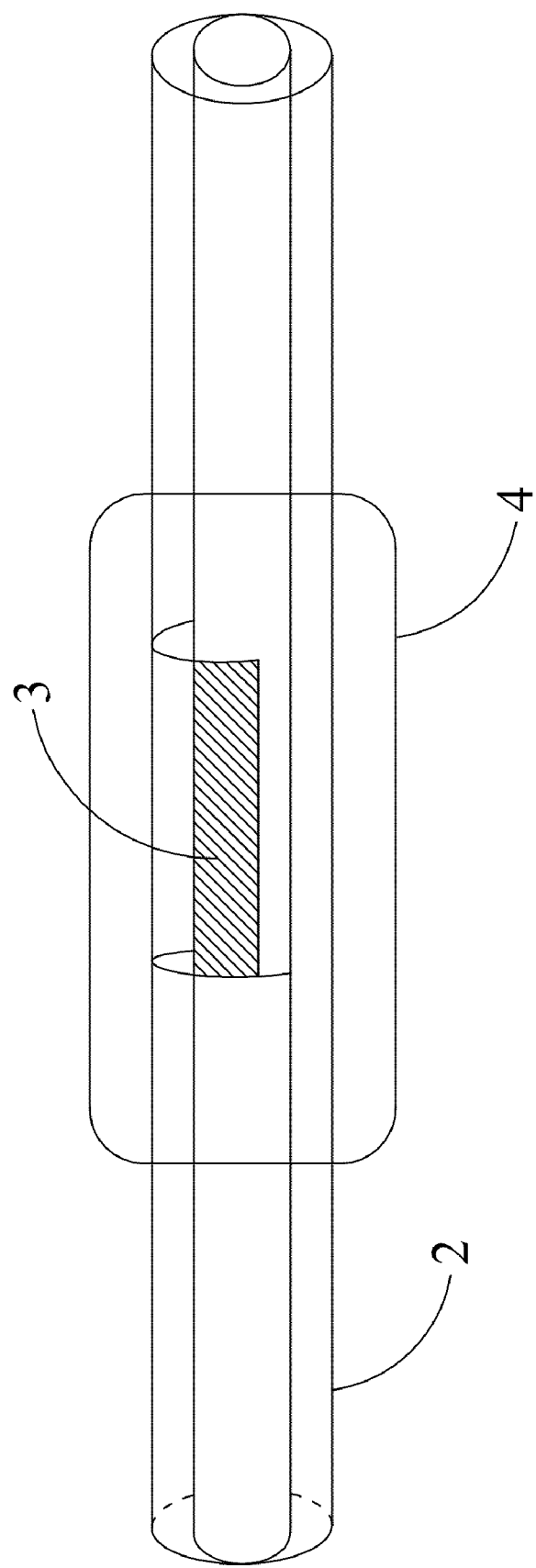
FIG. 4B is a schematic view of partially removing the cladding in a certain region of an optical fiber of a FO-LPR sensing device in accordance with the present invention.
Figure 4C:
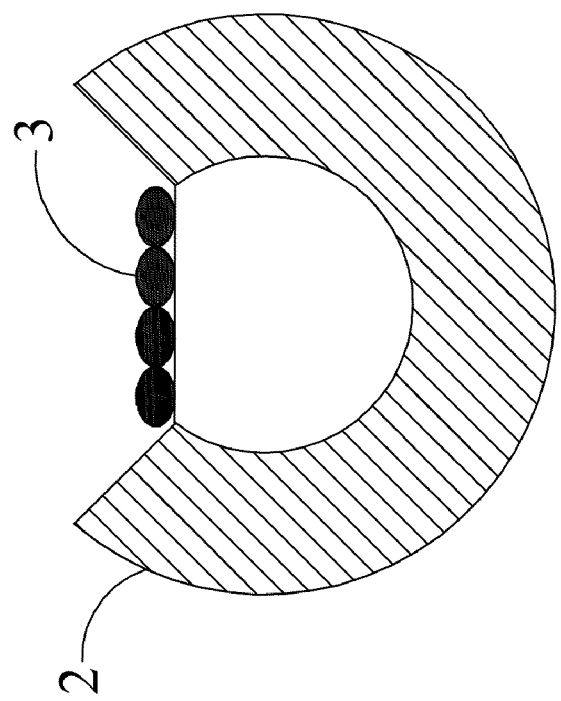
FIG. 4C is a cross-sectional view of partially removing the cladding in a certain region of an optical fiber of a FO-LPR sensing device in accordance with the present invention.
Figure 4C:
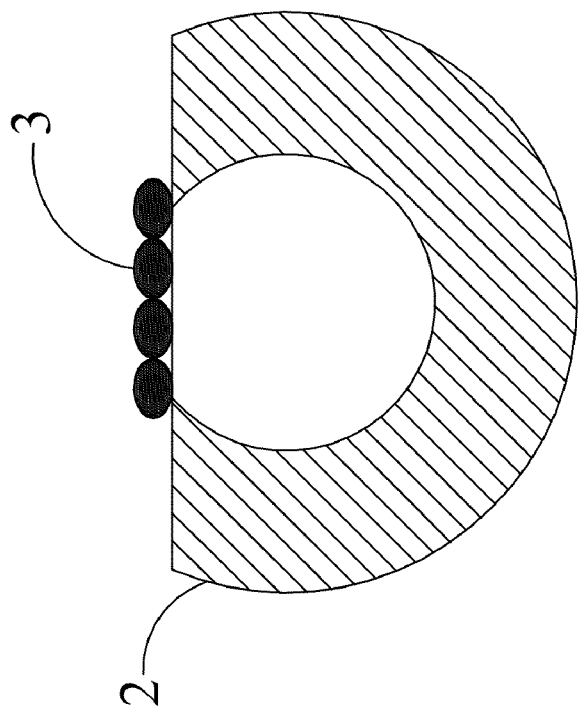
Figure 4D:
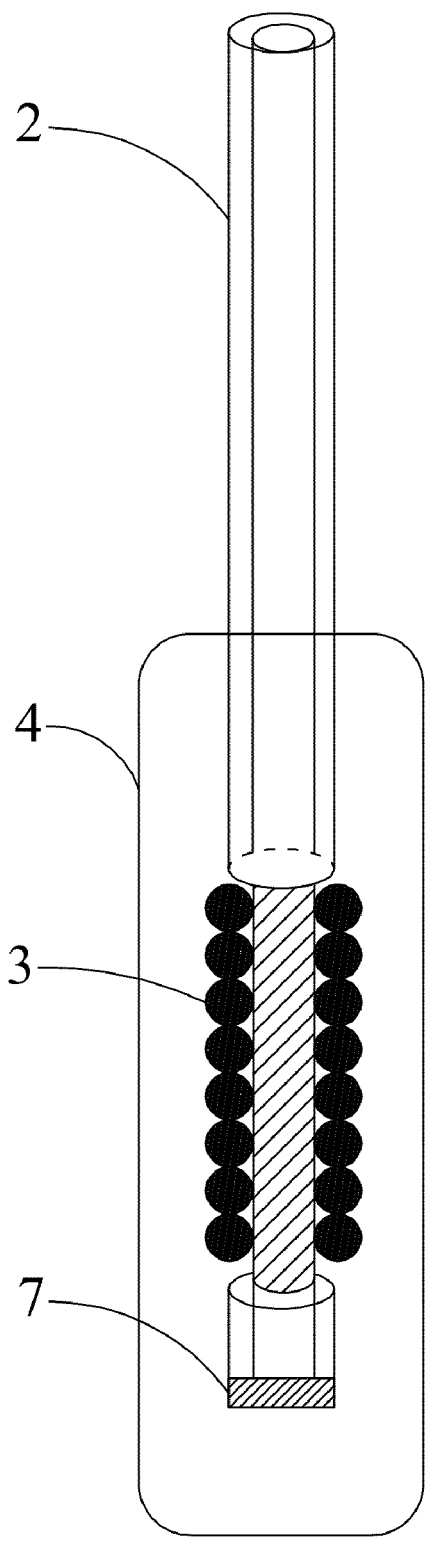
FIG. 4D is a schematic view of a sensing probe with a mirror coating coated at an end of an optical fiber of a FO-LPR sensing device in accordance with the present invention.
Figure 4E:
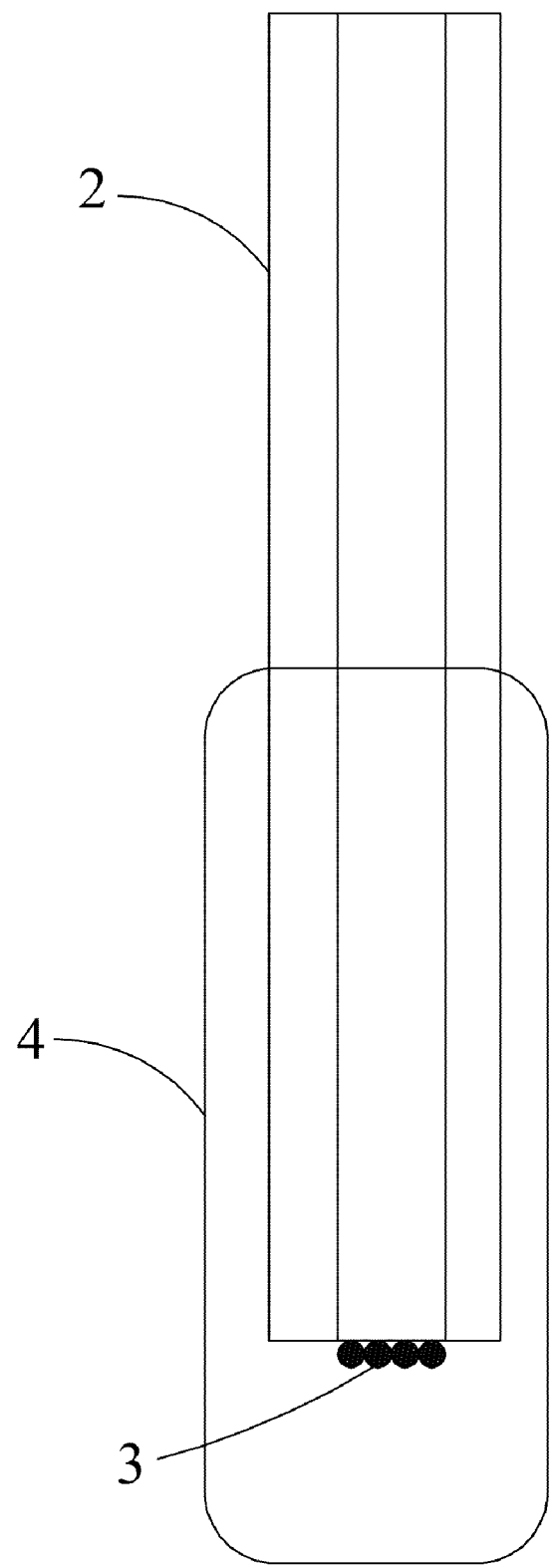
FIG. 4E is a schematic view of a sensing probe with a noble metal nanoparticle layer modified at an end of an optical fiber of a FO-LPR sensing device in accordance with the present invention.
Figure 4F:
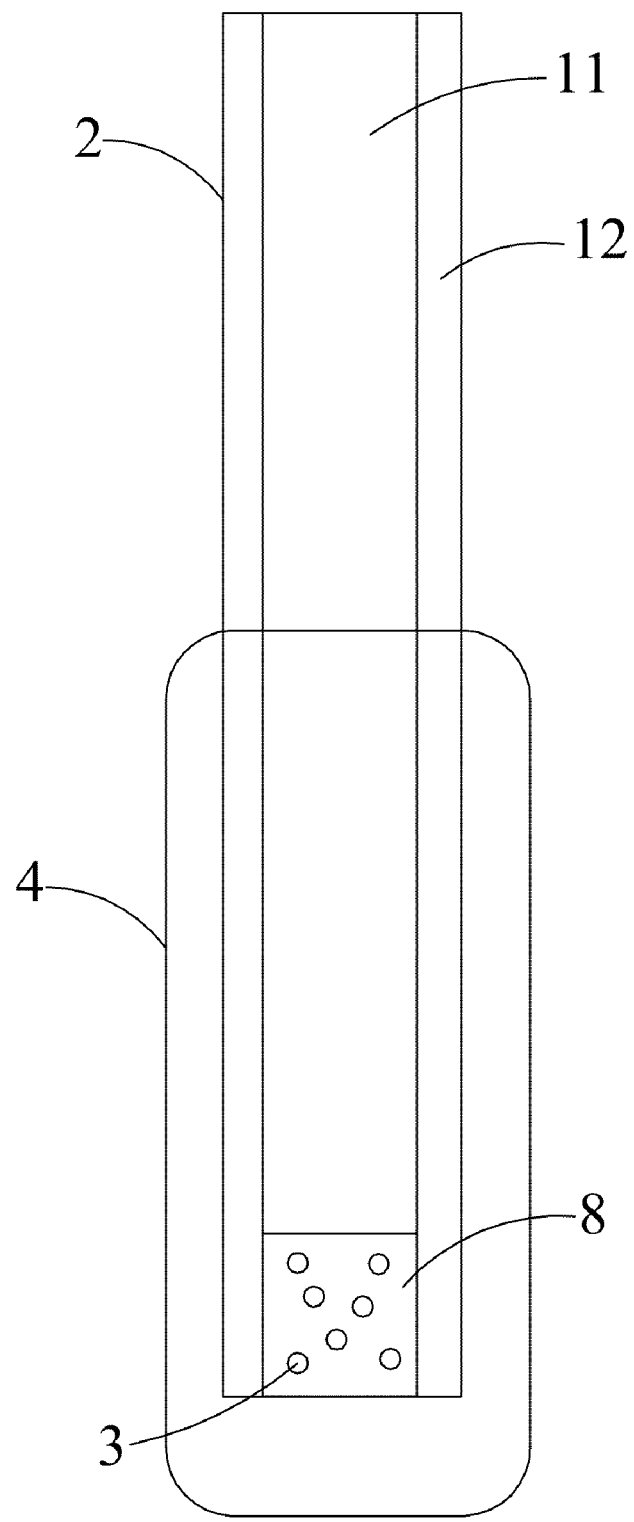
FIG. 4F is a schematic view of sensing probe with a porous material filled in a hollow core and noble metal nanoparticles further modified at an end of an optical fiber of a FO-LPR sensing device in accordance with the present invention.
Figure 4G:
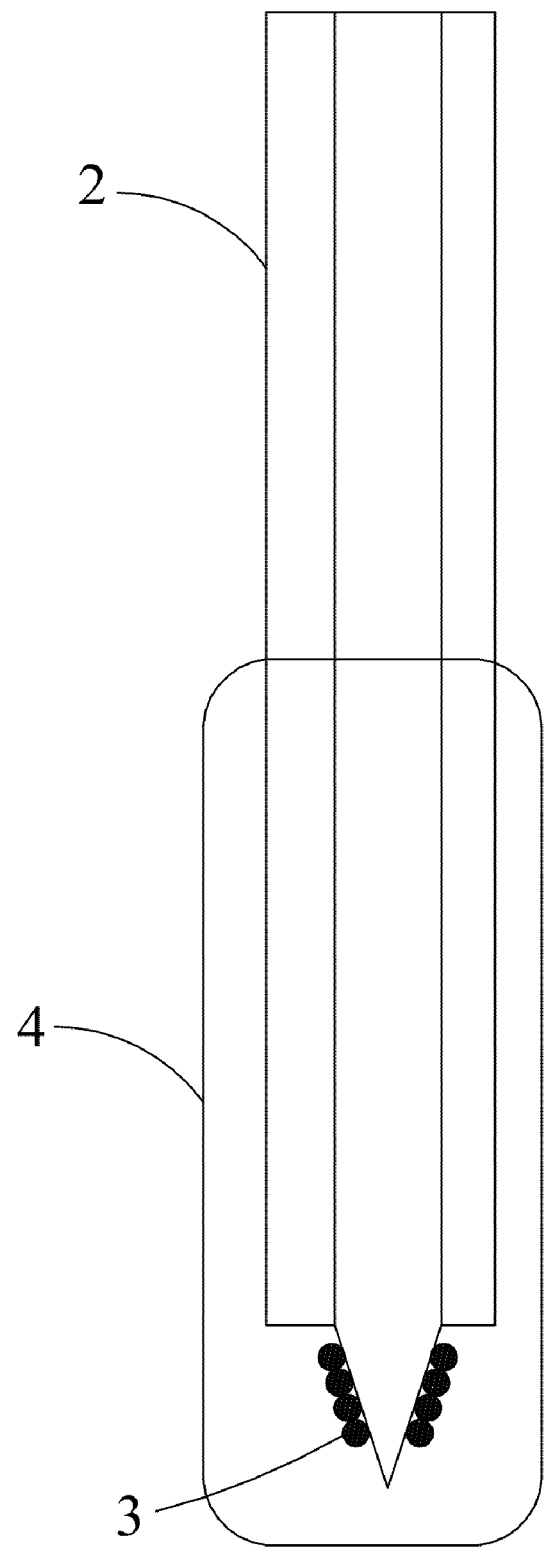
FIG. 4G is a schematic view of a sensing probe with a noble metal nanoparticle layer modified at an end of an optical fiber of a FO-LPR sensing device in accordance with the present invention.

With reference to FIG. 4 for schematic views of an optical fiber of a FO-LPR sensing device in accordance with the present invention, the optical fiber may have the entire cladding in a certain region removed (as shown in FIG. 4A), or a portion of cladding in a certain region removed (as shown in 4B), and its cross-sectional views are shown in FIG. 4C. In the design of the later, the optical fiber reserves a portion of the cladding uninterrupted, such that the fragile optical fiber core may have more physical support to give a better mechanical strength (such as the D-Fiber structure is an example of this design). It is a very good choice to use the design as shown in FIG. 4B for developing a smaller FO-LPR sensing device. With reference to FIG. 4D for a schematic view of a sensing probe with a mirror coating coated at an end of an optical fiber of a FO-LPR sensing device in accordance with the present invention, the mirror coating 7 is provided for reflecting a light beam, such that when the sensing probe is dipped in a liquid sample or pierced into a specific object, the test is completed. Obviously, such a sensing probe with a mirror coating is suitable to be used as part of an instrument for instant analysis or even further medical treatment. With reference to FIG. 4E for a schematic view of a sensing probe with a noble metal nanoparticle layer modified at an end of an optical fiber of a FO-LPR sensing device in accordance with the present invention, a noble metal nanoparticle layer 3 is disposed onto an end of the optical fiber 2, and the intensity of a scattered or reflected light signal is used for sensing. In this structure, the optical fiber still has an intact cladding, and thus the optical fiber has a very good mechanical strength. With reference to FIG. 4F for a schematic view of sensing probe with a porous material 8 filled in a hollow core 11 and noble metal nanoparticles further modified at an end of an optical fiber of a FO-LPR sensing device in accordance with the present invention, the hollow portion of the core 11 at the end section of the optical fiber 2 is etched, and the cladding 12 at the optical fiber 2 is maintained, and then the porous material 8 (such as sol-gel) is filled into this space, and finally the noble metal nanoparticle layer 3 is disposed onto the surface of the porous material 8 to complete the structure of such probe. The property of the porous material is intended for improving the mass transfer of the analyte, while the advantage of a large surface area of the material is intended for providing a higher number of immobilized noble metal nanoparticles to achieve a better sensing effect. With reference to FIG. 4G for a schematic view of a sensing probe with a noble metal nanoparticle layer 3 modified at an end of an optical fiber of a FO-LPR sensing device in accordance with the present invention, a chemical or mechanical procedure is used for making a tapered optical fiber, and the noble metal nanoparticle layer 3 is disposed onto the tapered end of the optical fiber 2 to facilitate the collection of fluorescent light or surface-enhanced Raman scattering light produced after the interaction of the incident light with the noble metal nanoparticles, and signals are collected at the proximal end of the optical fiber.

Figure 5:
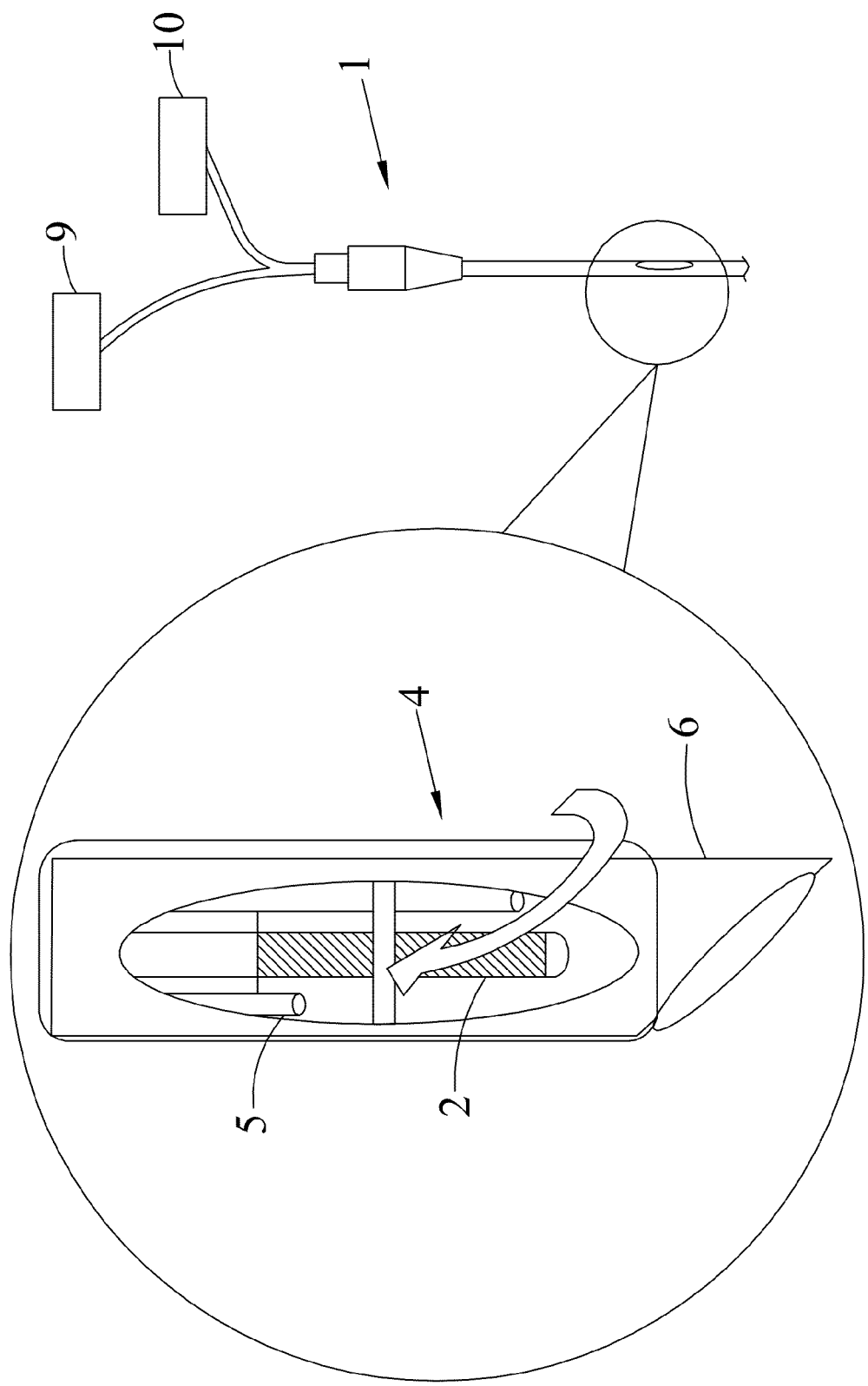
FIG. 5 is a schematic view of a FO-LPR sensing system in accordance with a fourth preferred embodiment of the present invention.

With reference to FIG. 5 for a schematic view of a FO-LPR sensing system in accordance with a fourth preferred embodiment of the present invention, the FO-LPR sensing system comprises a FO-LPR sensing device 1, a light source 9 and a detector 10, and the light source 9 provides a light beam entered into the FO-LPR sensing device 1, and the detector 10 receives an emergent light from the FO-LPR sensing device 1 to generate a detected signal. The light source may be a laser beam or a light emitting diode (LED), and the detector may be a photodiode, a phototransistor, a photomultiplier (PMT) or a charge coupling device (CCD). Although the FO-LPR probe type sensor has an excellent sensing capability, a serious interference by a non-specific attachment often occurs in the application to analysis of a real sample, since the composition of the real sample is very complicated and includes interfering substances such as blood cells, cell debrises and fibers, which have a chance to be covered onto the surface of the LPR optical fiber 2 and result in a serious error to the detected signal. In view of this issue, we combine a probe type FO-LPR sensing system with microdialysis and use a steel needle with holes as a component for the physical support. In an application of the microdialysis, such component provides a selective sampling capability, and together with the high sensing capability of the FO-LPR, may serve as a medical sensing device for in vivo analysis. Since a system with the aforementioned components includes liquid ducts, they are used for sampling the desired analyte and may also be used to introduce a medicine. If necessary, reagents may be introduced to regenerate the FO-LPR sensor. By the determination of the FO-LPR signal, we may know about the related information about a patient's conditions, and appropriate dosage of a medicine may be injected to achieve the expected effect of a medical treatment.

Figure 6:
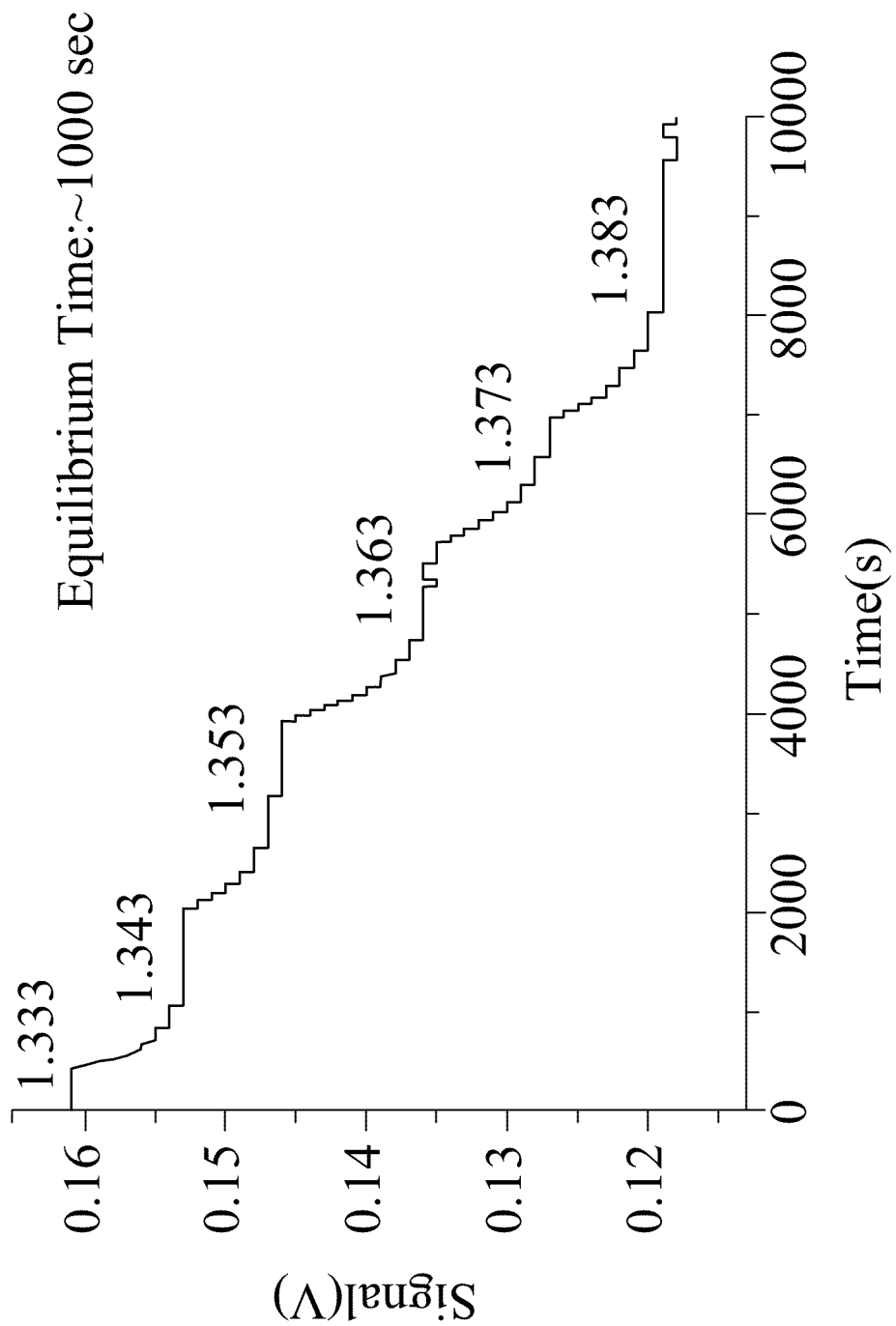
FIG. 6 is a graph of signal versus time in aqueous samples with different refractive indexes by a FO-LPR sensing system and a filter film layer in accordance with the present invention.

With reference to FIG. 6 for a graph of signal versus time of a detected change of solution refractive index by a FO-LPR sensing system which includes a filter film layer in accordance with the present invention, we put in surcose solution with different refractive indexes into a sample container in this experiment, the effect of each sample on the LPR signal is studied. With the microdialysis membrane (having a MWCF: 100 kDa), the mass transfer of a stagnant sample through the microdialysis membrane is limited, and thus it is necessary to provide a method to increasing the mass transfer rate. Thus, a sensing system based on the principle of microdialysis is used, and its overall structure is shown in FIG. 2. Experimental results show that the higher the solution refractive index is, the less is the drop of FO-LPR signal, and a relatively long equilibrium times of about 1000 seconds are required to reach a steady state.

Figure 7A:
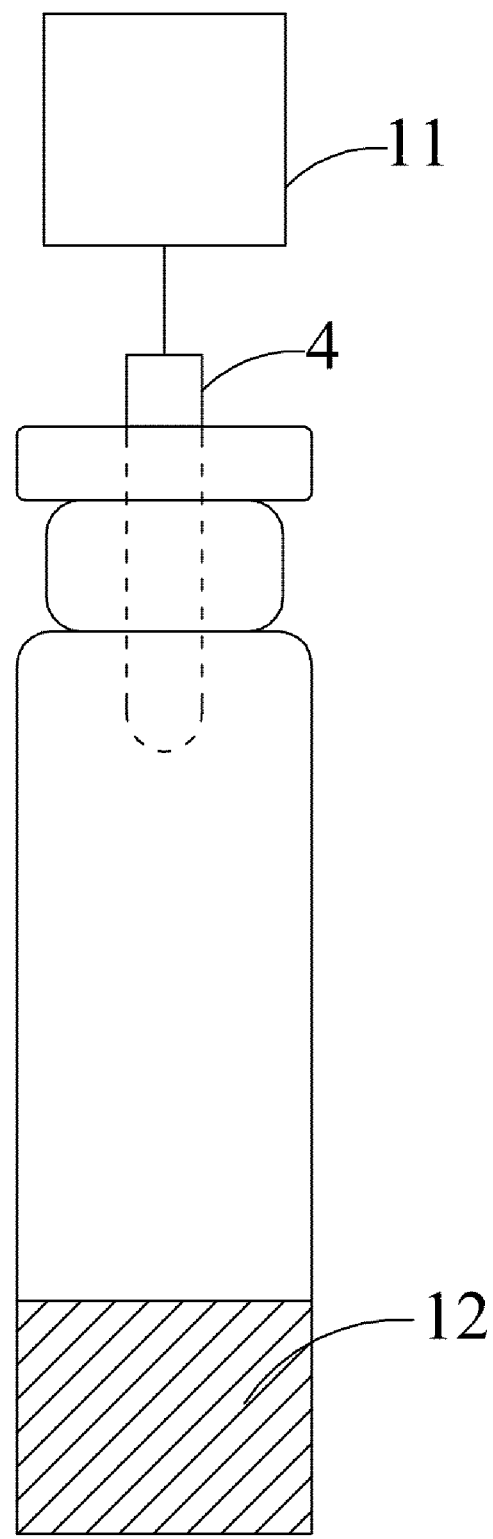
FIG. 7A is a schematic view of an aqueous sample containing polystyrene microspheres as an interfering substance that is filtered through a filter film layer to form a clear aqueous solution in accordance with the present invention.
Figure 7B:
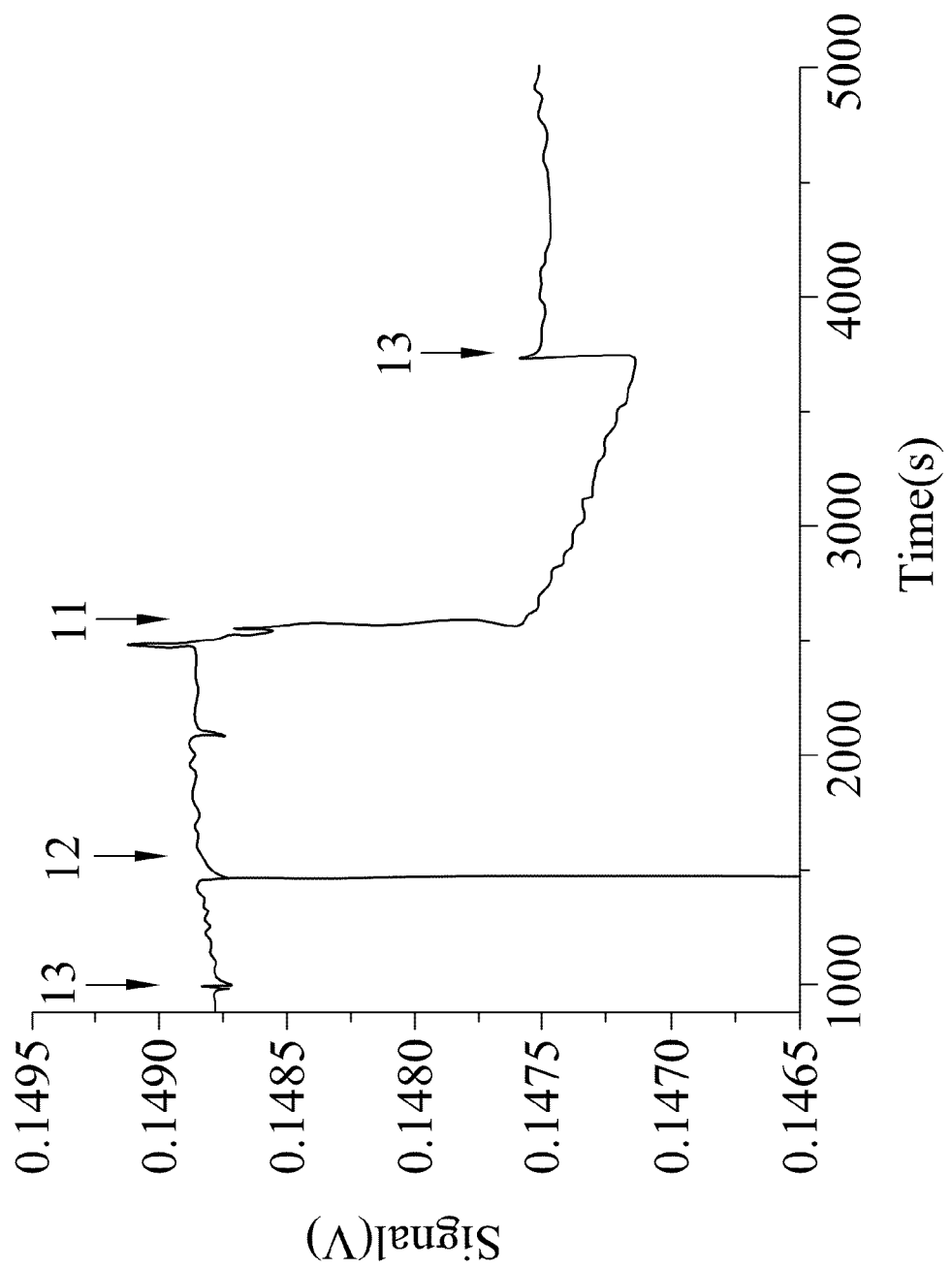
FIG. 7B is a graph of signal versus time by a FO-LPR sensing system of the present invention with a sample containing polystyrene microspheres as an interfering substance.
Figure 7C:
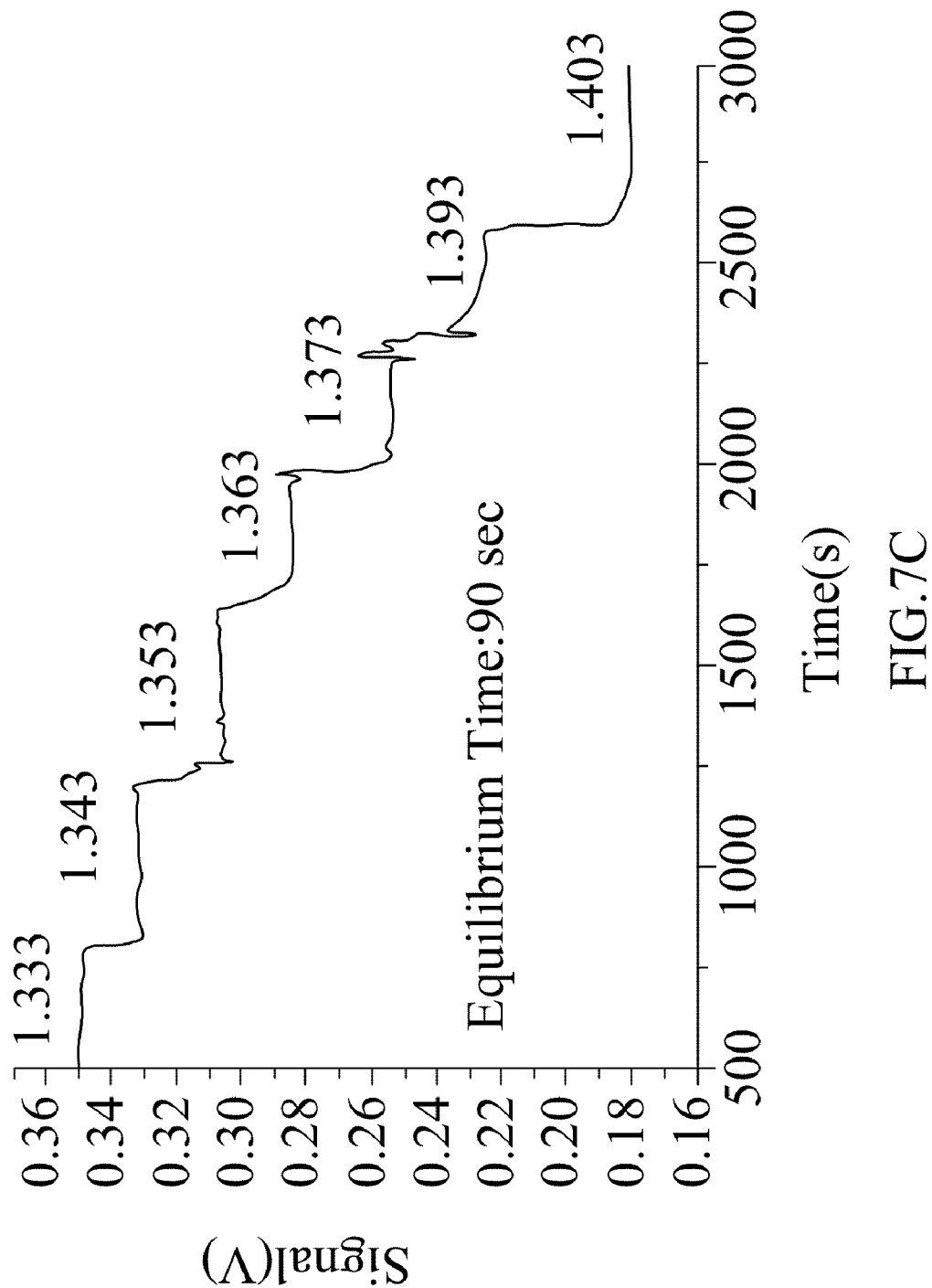
FIG. 7C is a graph of signal versus time in aqueous samples with different refractive indexes and containing polystyrene microspheres as an interfering substance by a FO-LPR system of the present invention.

With reference to FIG. 7A for a schematic view of an aqueous sample containing polystyrene (PS) microspheres as an interfering substance that is filtered through a filter film layer to form a clear aqueous solution in accordance with the present invention, the interfering substance is PS microspheres wherein the surface of the PS microspheres carries a negative charge, and thus the PS microspheres will be suspended uniformly in the aqueous solution by electrostatic repulsions. There are three main types of interferences by the PS microspheres to the LPR sensor: Firstly, the PS microspheres are relatively large particles, and thus the PS microspheres will be deposited on a bottom surface while sitting still; secondly, the PS microspheres will be attached onto the gold nanoparticle surface through hydrophobic interaction; and thirdly, the PS microspheres solution is in a white color, and thus the energy distribution of an optical waveguide will be changed. An upper layer liquid as shown in FIG. 7A is a PS microspheres solution 11 having a concentration of $2.18 \times 10^9$ beads/mL, and shows a clear filtrate 12 after being passed and filtered through a filter film 4 with a pore diameter of 200 nm. In FIG. 7B, a temporal response of a FO-LPR system to a PS microspheres solution 11 and its filtrate 12 is shown, wherein the FO-LPR system initially is in an equilibrium state in pure water 13, and when the clear filtrate 12 as shown in FIG. 7A is injected into the sensing system, no change of the LPR signal is found. If the PS microspheres solution 11 is injected directly into the system, then a drastic drop of signal will be observed. This is because the white PS microspheres solution 11 affects the energy of the evanescent wave of the optical waveguide and causes a change of light intensity to the detector. In addition, we may observe a gradual drop of the LPR signal. This may be caused by the PS microspheres that start being deposited on the surface of the gold nanoparticles. Finally, we inject pure water 11 into the system for several times, in hope of rinsing and cleaning the surface of the sensing optical fiber. However, we may find that the LPR signal has already deviated from its original equilibrium signal, and it indirectly shows that the PS microspheres are covered onto the surface of gold nanoparticles to a certain extent. This basic research also indicates that the use of a filter film with a pore diameter of 200 nm may isolate the sensing optical fiber from being interfered by the PS microspheres with a particle diameter of 500 μm. In a further experiment, a PS microspheres solution 11 having a concentration of $2.18 \times 10^8$ beads/mL is used as a solute for each sample with a different refractive index, and thus these samples have a cream white color. With reference to FIG. 7C for a graph of signal versus time of aqueous samples containing PS microspheres as an interfering substance and having different refractive indexes detected by a FO-LPR system of the present invention, the purpose of this experiment is to show that the LPR sensor may perform analysis of turbid samples. In this experiment, unclear surcose solution samples with different refractive indexes and contain PS microspheres are injected into the sample container, and then a relation between signal output of the FO-LPR sensing system and solution refractive index is analyzed, and the result shows that the higher the refractive index is, the greater is the drop of the LPR signal, and a steady state will be achieved after approximately 90 seconds, indicating that the filter film with a larger pore size may expedite the mass transfer of an analyte in a sample through the filter film.

Figure 8A:
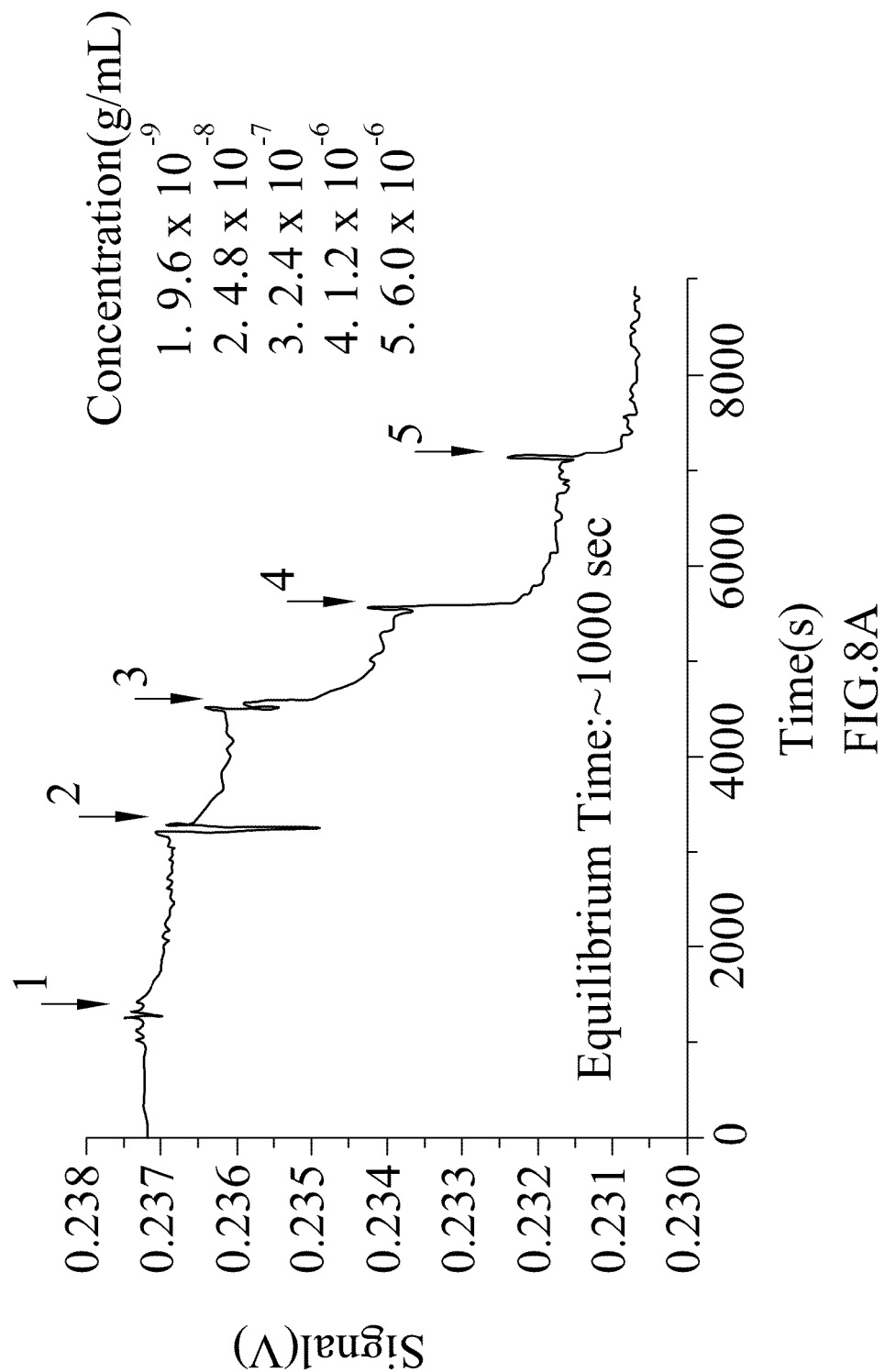
FIG. 8A is a graph of signal versus time in samples of different concentrations of streptavidin and containing polystyrene microspheres as an interfering substance by a FO-LPR sensing system which includes a filter film layer of the present invention.
Figure 8B:
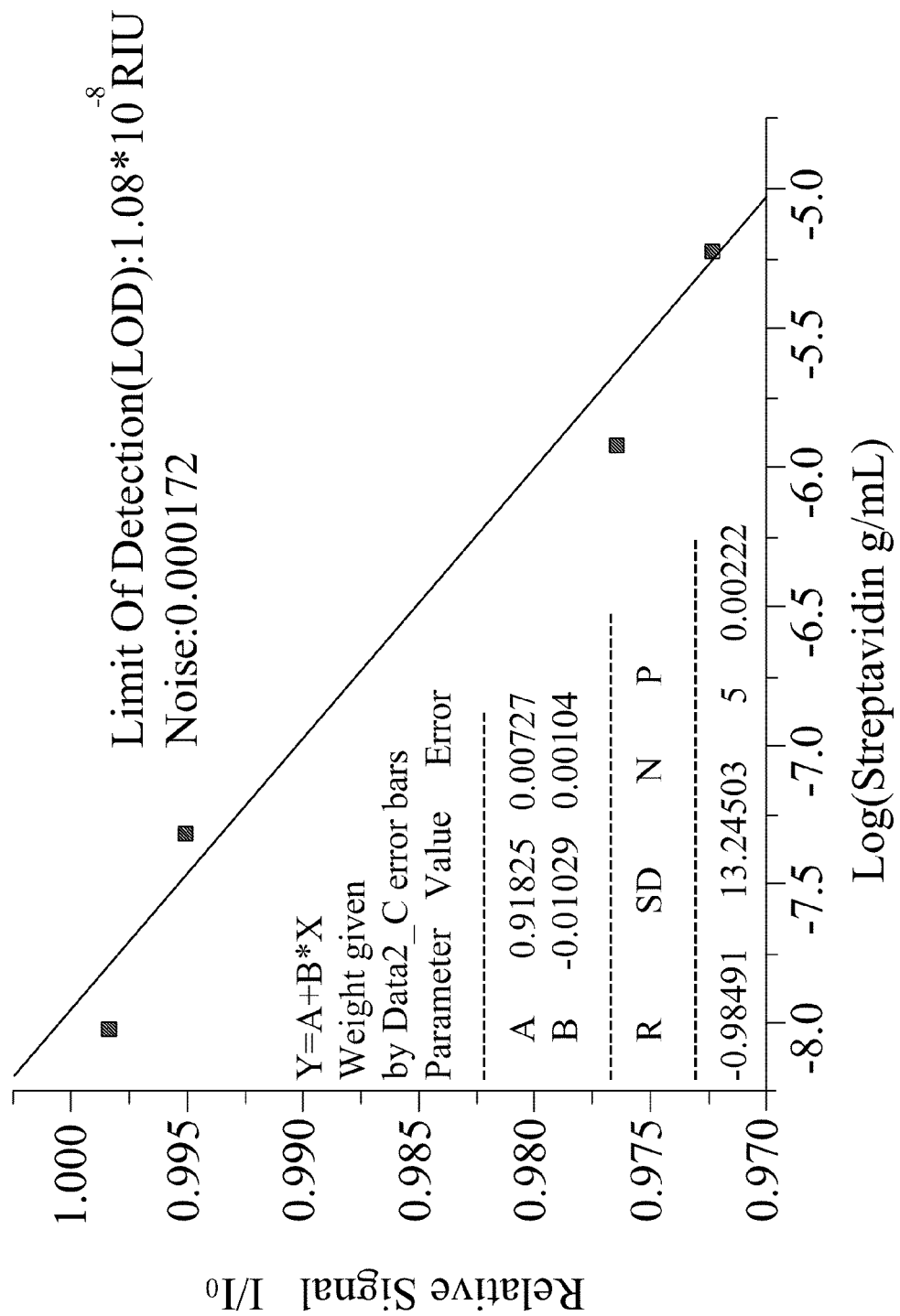
FIG. 8B is a calibration graph of relative signal versus log (concentration) of streptavidin samples containing polystyrene microspheres as an interfering substance by a FO-LPR sensing system which includes a filter film layer of the present invention.

With reference to FIG. 8A for a graph of signal versus time of biochemical molecules detected in an environment with an interfering substance by a FO-LPR sensing system of the present invention, we used the model of vitamin H-streptavidin (biotin-streptavidin) pair for testing in order to verify that the sensing system comprised of the LPR optical fiber and the filter film has a biochemical sensing capability. The experimental method uses vitamin H to modify the gold nanoprticle surface on the LPR optical fiber, and attempts to determine streptavidin in samples filtered by the filter film layer. The filter film layer used in the experiment comprises cellulose and has a pore diameter of 200 nm, and thus theoretically, only the streptavidin (~4 nm) having a molecular weight of 60 kDa may be able to pass through the film successfully, and finally detected by the optical fiber sensor. With reference to FIG. 8B for a graph of relative signal versus log (concentration) by a FO-LPR sensing system of the present invention, when samples of streptavidin from low concentration to high concentration and with PS microspheres as an interfering substance are injected into the FO-LPR sensing system, the FO-LPR signal also shows that the higher the concentration of the analyte is, the greater is the drop of the signal, and the injection of each new sample requires approximately 1000 seconds to reach steady state. The signal reaching the steady state is used in a plot of relative signal versus the log of concentration, and the correlation coefficient (R) of the plot is equal to 0.9849. The noise of the system is $1.7 \times 10^{-3}$, and finally we may derive that the detection limit is $1.08 \times 10^{-8}$ g/mL ($1.8 \times 10^{-10}$ M).

Figure 9:
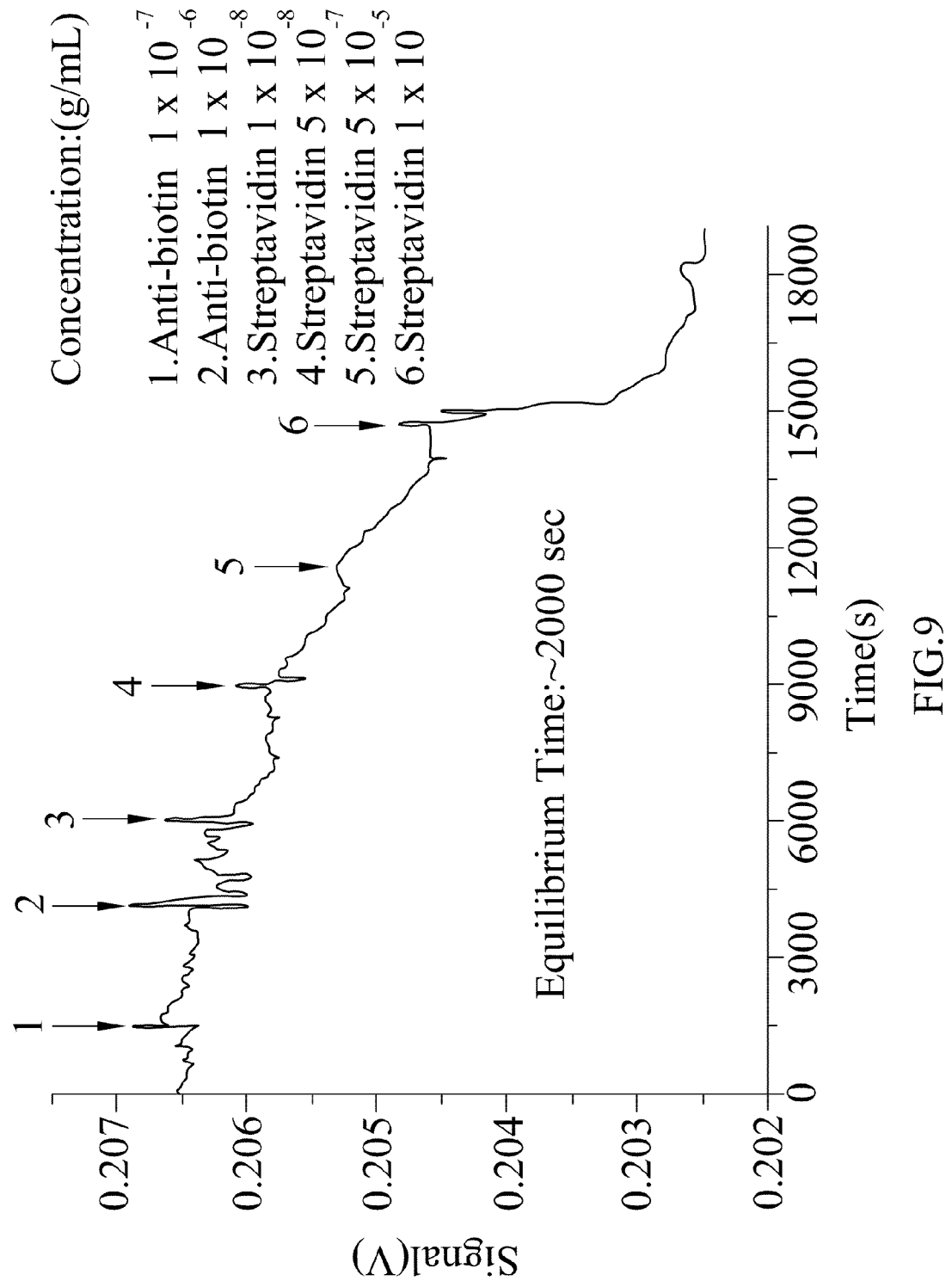
FIG. 9 is a graph of signal versus time with samples containing anti-biotin antibody or streptavidin of various concentrations by a FO-LPR sensing system which includes a filter film layer of the present invention.

With reference to FIG. 9 for a graph of signal versus time of samples of streptavidin or anti-vitamin H (anti-biotin) of various concentrations by a FO-LPR sensing system which includes a filter film layer (MWCO=100 kDa) of the present invention, a sample solution of anti-vitamin H with a molecular weight of 150 kDa is injected into the sample container in this experiment, and it is expected that the filter film has a screening capability for anti-vitamin H. We then replace the sample with a streptavidin solution of a different concentration. Since the molecular weight is just 60 kDa, therefore it is expected that streptavidin will pass through the filter film and cause a change of FO-LPR signal. FIG. 9 shows the experimental results, wherein No. 1 and No. 2 are samples of anti-vitamin H with concentrations of $1 \times 10^{-7}$ g/mL and $1 \times 10^{-6}$ g/mL respectively, and the results show hat the injection of anti-vitamin H samples will not cause a change of the FO-LPR signal. However, the samples of streptavidin from No. 3 to No. 6 show that vitamin H molecules on the gold nanoparticle surface recognize streptavidin and significant signal changes are observed. The experimental result shows that the use of the filter film (with MWCO of 100 kDa) may hinder the higher molecular weight anti-vitamin H (150 kDa) from entering the sensing region, and may allow the lower molecular weight streptavidin (60 kDa) to pass through, and finally the FO-LPR optical fiber may be used for the sensing purpose.

The present invention focuses on how to use a rapid and simple apparatus and method for the FO-LPR sensing device and its system without tedious sample pre-treatment, and chooses a selective material for analysis according to a property of a sample, so as to maximize the sensing effect. For example, a filter film may isolate large particles, organisms or macromolecules from entering the sensing area, so that the filtrate through the filter film layer becomes simpler, and the interfering substances in a sample will be reduced significantly. Finally, detection of a specific analyte in a sample by the FO-LPR sensing device and its system is achieved by the selectivity of the recognition unit on the sensor surface.

While the invention has been described by means of specific embodiments, numerous modifications and variations could be made thereto by those skilled in the art without departing from the scope and spirit of the invention set forth in the claims.

What is claimed is:

1. A fiber-optic localized plasmon resonance (FO-LPR) sensing device, comprising:
   at least one optical fiber;
   a noble metal nanoparticle layer, disposed on the optical fiber; and
   a filter film layer, having a porous material, and encloses the optical fiber;
   wherein the porous material comes with a pore diameter or a property selected according to a feature of a sample while an interfering substance in the sample is isolated.

2. The FO-LPR sensing device of claim 1, wherein the optical fiber has a region with an entire cladding removed, or the optical fiber has a region with a portion of the cladding removed, and the cladding removed area of the optical fiber is a sensing area.

3. The FO-LPR sensing device of claim 1, wherein the noble metal nanoparticle layer interacts with an incident light to produce a fluorescent light or a surface-enhanced Raman scattering light.

4. The FO-LPR sensing device of claim 1, wherein the filter film layer comes with the pore diameter from 0.2 μm to 20 μm, a pore density from $4\times10^4$ $cm^{-2}$ to $20\times10^4$ $cm^{-2}$, a thickness from 50 μm to 100 μm or a molecular weight cut off (MWCO) smaller than or equal to 500 kDa.

5. The FO-LPR sensing device of claim 1, further comprising a rigid frame with an opening on its wall and disposed between the filter film layer and the optical fiber, for providing a physical support and guiding the sample to a specific sensing area.

6. The FO-LPR sensing device of claim 1, further comprising at least one duct disposed inside a region enclosed by the filter film layer for introducing a perfusion liquid or discharging the perfusion liquid.

7. The FO-LPR sensing device of claim 1, wherein the optical fiber includes a mirror coating coated at an end of the optical fiber for reflecting a light signal.

8. The FO-LPR sensing device of claim 1, wherein the noble metal nanoparticle layer is disposed onto an end of the optical fiber for scattering or reflecting a light signal.

9. The FO-LPR sensing device of claim 1, wherein the optical fiber forms a hollow cavity at an end of the optical fiber by etching a portion of a core, and the hollow cavity is filled by the porous material for disposing noble metal nanoparticles on the surface of the porous material.

10. A fiber-optic localized plasmon resonance (FO-LPR) sensing system, comprising:
    a FO-LPR sensing device, comprising:
        at least one optical fiber;
        a noble metal nanoparticle layer, disposed on the optical fiber; and
        a filter film layer, having a porous material, and encloses the optical fiber;
    a light source, for providing a light beam entered into the FO-LPR sensing device; and
    a detector, for receiving an emergent light from the FO-LPR sensing device to generate a detected signal;
    wherein the porous material comes with a pore diameter or a property selected according to a feature of a sample, while an interfering substance in the sample is isolated.

11. The FO-LPR sensing system of claim 10, wherein the optical fiber has a region with an entire cladding removed, or the optical fiber has a region with a portion of the cladding removed, and the cladding removed area of the optical fiber is a sensing area.

12. The FO-LPR sensing system of claim 10, wherein the noble metal nanoparticle layer interacts with an incident light to produce a fluorescent light or a surface-enhanced Raman scattering light.

13. The FO-LPR sensing system of claim 10, wherein the filter film layer comes with the pore diameter from 0.2 μm to 20 μm, a pore density from $4\times10^4$ $cm^{-2}$ to $20\times10^4$ $cm^{-2}$, a thickness from 50 μm to 100 μm or a molecular weight cut off (MWCO) smaller than or equal to 500 kDa.

14. The FO-LPR sensing system of claim 10, further comprising a rigid frame with an opening on its wall and disposed between the filter film layer and the optical fiber, for providing a physical support and introducing the sample to a specific sensing area.

15. The FO-LPR sensing system of claim 10, wherein the optical fiber includes a mirror coating coated at an end of the optical fiber for reflecting a light signal.

16. The FO-LPR sensing system of claim 10, wherein the noble metal nanoparticle layer is disposed onto an end of the optical fiber for scattering or reflecting a light signal.

17. The FO-LPR sensing system of claim 10, wherein the optical fiber forms a hollow cavity at an end of the optical fiber by etching a portion of a core, and the hollow cavity is filled by the porous material for disposing noble metal nanoparticles onto the surface of the porous material.

18. The FO-LPR sensing system of claim 10, wherein the light source is a laser or a light emitting diode (LED).

19. The FO-LPR sensing system of claim 10, wherein the detector is a photodiode, a phototransistor, a photomultiplier (PMT) or a charge coupling device (CCD).

20. The FO-LPR sensing system of claim 10, further comprising at least one duct or a pump, and the duct is disposed inside a region enclosed by the filter film layer for introducing a perfusion liquid or discharging the perfusion liquid, and the pump draws the perfusion liquid through the duct into a region enclosed by the filter film layer or removes the perfusion liquid through the duct from a region enclosed by the filter film layer.

* * * * *